United States Patent [19]

Cadet et al.

[11] Patent Number: 5,138,149
[45] Date of Patent: Aug. 11, 1992

[54] APPARATUS AND METHOD FOR MONITORING RADIANT ENERGY SIGNALS WITH VARIABLE SIGNAL GAIN AND RESOLUTION ENHANCEMENT

[75] Inventors: Raymond J. Cadet; Hung-Nan Chao; Sing-wing Hui; Eric Bogatin, all of San Jose; Steven C. Leach, Santa Clara, all of Calif.

[73] Assignee: Xinix, Inc., Santa Clara, Calif.

[21] Appl. No.: 578,538

[22] Filed: Sep. 5, 1990

[51] Int. Cl.⁵ .............................................. H01J 40/14
[52] U.S. Cl. ................................. 250/214 AG; 250/559
[58] Field of Search .......... 250/214 A, 214 AL, 562, 250/214 C, 561, 214 B, 214 AG, 559, 560, 571; 354/298

[56] References Cited

U.S. PATENT DOCUMENTS

| | | |
|---|---|---|
| 4,061,925 | 12/1977 | van der Gaag et al. ........ 250/214 B |
| 4,136,940 | 1/1979 | Lin . |
| 4,462,860 | 7/1984 | Szmanda . |
| 4,469,424 | 9/1984 | Matsui et al. . |
| 4,569,717 | 2/1986 | Ohgami et al. . |
| 4,647,172 | 3/1987 | Batchelder et al. . |
| 4,673,807 | 6/1987 | Kobayashi et al. ......... 250/214 AG |
| 4,791,286 | 12/1988 | Wall ................................ 250/214 A |
| 5,015,839 | 5/1991 | Tanikoshi .................... 250/214 AG |

Primary Examiner—David C. Nelms
Assistant Examiner—K. Shami
Attorney, Agent, or Firm—Skjerven, Morrill, MacPherson, Franklin & Friel

[57] ABSTRACT

A sensor board for use with an endpoint controller which monitors light intensity is provided. The sensor board can provide a dynamic range of up to five million because a constant current driver and phase sensitive detector help eliminate noise from the detected signal. The sensor board can also subtract a DC voltage offset from the detected signal and amplify the difference to provide increased resolution of small changes in the detected signal.

27 Claims, 8 Drawing Sheets

Microfiche Appendix Included
(66 Microfiche, 1 Pages)

Fig. 1

INTERFEROGRAM OF PPHOTORESIST DEVELOPMENT PROCESS

APPARATUS AND METHOD FOR MONITORING RADIANT ENERGY SIGNALS WITH VARIABLE SIGNAL GAIN AND RESOLUTION ENHANCEMENT

CROSS REFERENCE TO MICROFICHE APPENDIX

Appendix A, which is part of the present disclosure, is a microfiche appendix consisting of 1 sheet of microfiche with a total of 67 frames. Microfiche Appendix A is a listing of a computer program which is described more completely below for use with a sensor board according to this invention.

FIELD OF THE INVENTION

This invention relates to a sensor board which facilitates accurate detection of the end of certain operations (such as etching, photoresist development or chemical reaction) in the processing of materials by detecting a change in the reflectivity or refractive index of the material and more particularly to an electronic circuit for use on such a sensor board.

BACKGROUND OF THE INVENTION

A controller for detecting the end of an operation (often called the "endpoint") on materials and particularly on semiconductor wafers will typically detect the endpoint by detecting a change in light being reflected or transmitted from the material. In one system for doing this an optical emitter such as a light-emitting diode (LED) produces light which strikes a wafer surface and is reflected back to a photodetector. In another system light produced by a reaction process is monitored by a detector and the rate of change of this light in certain frequency bands is used to detect the endpoint of an operation. In both cases the detected light intensity is a measure of the state of the material being processed. The state of the material being processed may be measured by the material's reflectivity or by the chemical constituents of the material or by the index of refraction of the material. A change in reflectivity indicates the process endpoint for metal etching, while the end of thin-film-interference oscillation in the detected light may signal the endpoint for dielectric etching and photoresist development.

Figure 1:
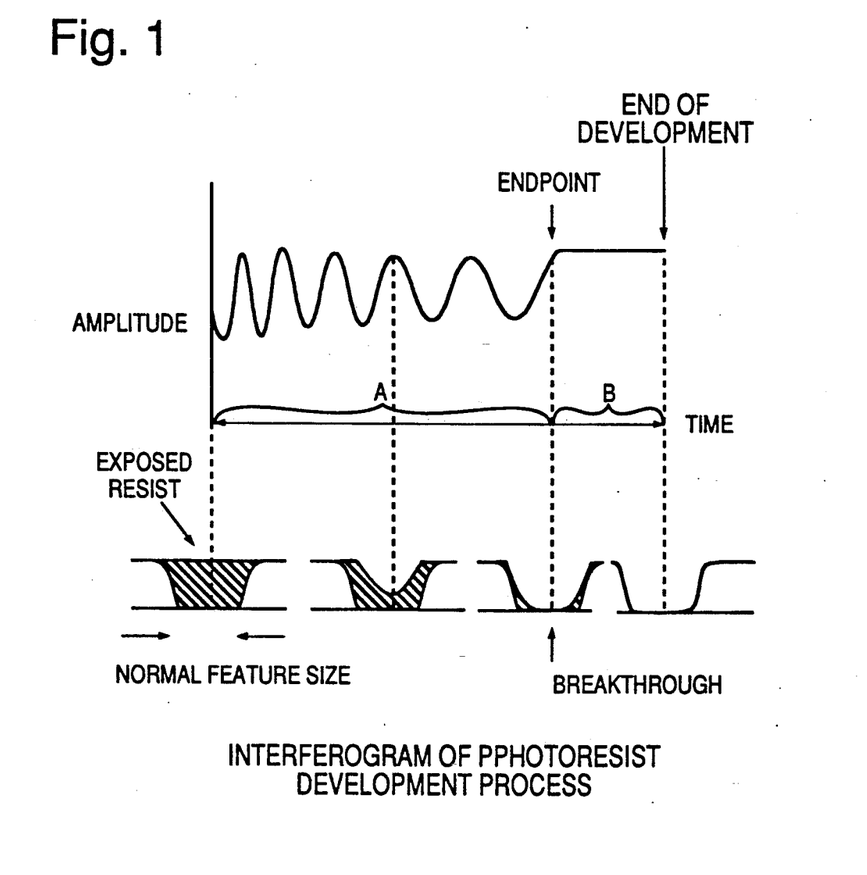
FIG. 1 illustrates how an interferogram produced by an endpoint controller varies as a layer of photoresist is developed.

During development and removal of photoresist or during dielectric etching, interference fringes are a direct indication of resist dissolution or dielectric removal. The breakthrough to the underlying substrate (which might be a semiconductor wafer surface, for example) that occurs when the photoresist or dielectric is removed is referred to as the endpoint and, as shown in FIG. 1, is recognizable as the point where the interference signal becomes nearly flat. The total process time consists of the time (A) which is required to reach breakthrough (endpoint), and any additional time (B) needed to clear out the resist or the dielectric completely. The time (B) is generally referred to as the overdevelopment period and will depend upon the nature of the material being removed. The total process time is equal to the sum of the time to endpoint plus the overdevelopment or overetch time. For simplicity, the phrase "overprocess time" will be used in this specification to mean either the overdevelopment time or the overetch time depending on whether a photoresist is being developed and thus removed or a layer of material is being removed.

The actual signals observed can, and in many cases will, vary drastically from an ideal interferogram pattern. Variations in reflectivity from the substrate layers (Si, Poly-Si, Al, $SiO_2$, $Si_3N_4$, etc.) die density, topography, substrate roughness, as well as process variables, will affect the strength and characteristics of the reflected signal.

Establishing precise endpoint time is essential in determining the start of the overprocess period, so that the total process time is tightly controlled. A reliable and accurate process control system must be able to recognize an endpoint under any variable signal conditions. For instance, in semiconductor processing where endpoint detection is important, wafer conditions and the wafer-to-sensor distance may vary. In order for the endpoint to be accurately detected, small changes in the reflected light intensity must be measured and changes in light intensity due to effects other than the process being monitored must be eliminated.

Endpoint detection sensors capable of meeting these stringent requirements can suffer from several problems. Ambient light can interfere with the detection of light reflected from the wafer. In addition, as the wafer spins during processing, the wafer may wobble or tilt, causing the reflected light intensity to vary. This artifact may also interfere with endpoint detection.

Sensor boards for processing the electrical signals produced by the photodetectors of endpoint detection sensors according to the prior art may only have a dynamic range of 4. In this case, strong signals caused by intense light reflected from the substrate may saturate the detection circuitry of the sensor board and prevent accurate recording of light intensities. Alternatively, weak signals and small signal changes may be too small for accurate measurement or detection if those weak signals cannot be adequately amplified. In addition, it may not be possible to adjust the sensor distance from the substrate surface to a convenient level to avoid, for instance, the developer dispense nozzle when only a limited dynamic range is available. A sensor placed far from a substrate will receive less intense light and unless the signal generated by that light can be adequately amplified, the signal may be too weak to provide accurate measurement.

SUMMARY OF THE INVENTION

A sensor board according to this invention can be used with an endpoint controller to provide the endpoint controller with greater dynamic range and greater programming flexibility. Broadly speaking, in accordance with this invention the sensor board automatically adjusts the gain of the electrical signal generated when a photodiode detects light reflected from a substrate so as to provide an output signal which can be more accurately analyzed to detect changes in the reflected light due to process changes.

The sensor board also automatically removes extraneous effects not related to the process such as noise and ambient light from the detected signal to facilitate the detection of changes in the reflected light. In addition, the sensor board of this invention can increase resolution of the detected signal by expanding the range over which changes in the signal are measured. By automatically adjusting gain, removing extraneous effects and increasing resolution, the sensor board in accordance with this invention aids in the accurate detection of small changes in the detected signal.

In one embodiment the gain is adjusted by automatically selecting one or more feedback resistors from a group of resistors which is one component of a current-to-voltage converter. A programmable gain amplifier on the sensor board is used in conjunction with the selectable feedback resistors, to achieve a selected dynamic range typically but not necessarily up to 500 million. With such a large dynamic range, an endpoint controller can automatically compensate for sensor-to-substrate distance variations from less than 1 inch to over 20 inches and variations in substrate surfaces, from highly reflective to very diffuse. Thus, the large dynamic range provided by a sensor board according to this invention allows accurate endpoint detection by an endpoint controller from both very strong and very weak signals.

A sensor board of this invention also minimizes sensitivity to stray noise and ambient light sources. A very low noise level is required to produce useful data from a signal which has been amplified up to 500 million times. A phase-sensitive detector filters some stray noise and subtracts that portion of the signal which is caused by ambient light from the total signal generated by a photodetector. A constant current driver decreases the variation of the LED output intensity due to ambient temperature changes to also reduce noise. Thus, the phase-sensitive detector and the constant current driver both aid in making the high dynamic range of this invention possible.

Only a small percentage variation in the detected signal may contain endpoint information. Once the gain is adjusted to bring the electrical signal to a high value, very small changes in the signal representing very small changes in the reflected light intensity can be measured with increased resolution after subtracting the DC portion of the signal and amplifying the difference. A digital-to-analog converter circuit supplies the DC offset and a programmable difference gain amplifier is used to subtract the DC component from the electrical signal and amplify the difference. After this processing, variations in the electrical signal signifying endpoint will be a much larger percentage of the signal and, thus, easier to accurately detect. The amplified difference signal is then digitized by a 12-bit analog-to-digital converter having a resolution of 2.5 millivolts. If a gain of 100 is applied after the DC component is subtracted, this resolution is actually $2.5 \times 10^{-5}$ volts. With a typical DC signal of 5 volts, a resolution of 1 part in 200,000 can be achieved using the sensor board of this invention.

According to one embodiment of this invention, two parallel channels are built into the sensor board so that two independent photodetectors can be used simultaneously and the signal resulting from each photodetector can be individually processed. This feature compensates for variations in the reflected light caused by substrate wobble as the substrate spins during processing. For example, if a photodetector is mounted on either side of the LED which transmits light to the substrate, then the average of the signals produced by each photodetector can decrease the endpoint controller's sensitivity to substrate wobble by decreasing oscillation in the resultant electrical signal.

The sensor board of this invention may also include circuits for calibration, diagnostic circuits and components for making the endpoint controller AT compatible.

DETAILED DESCRIPTION OF THE INVENTION

Figure 2:
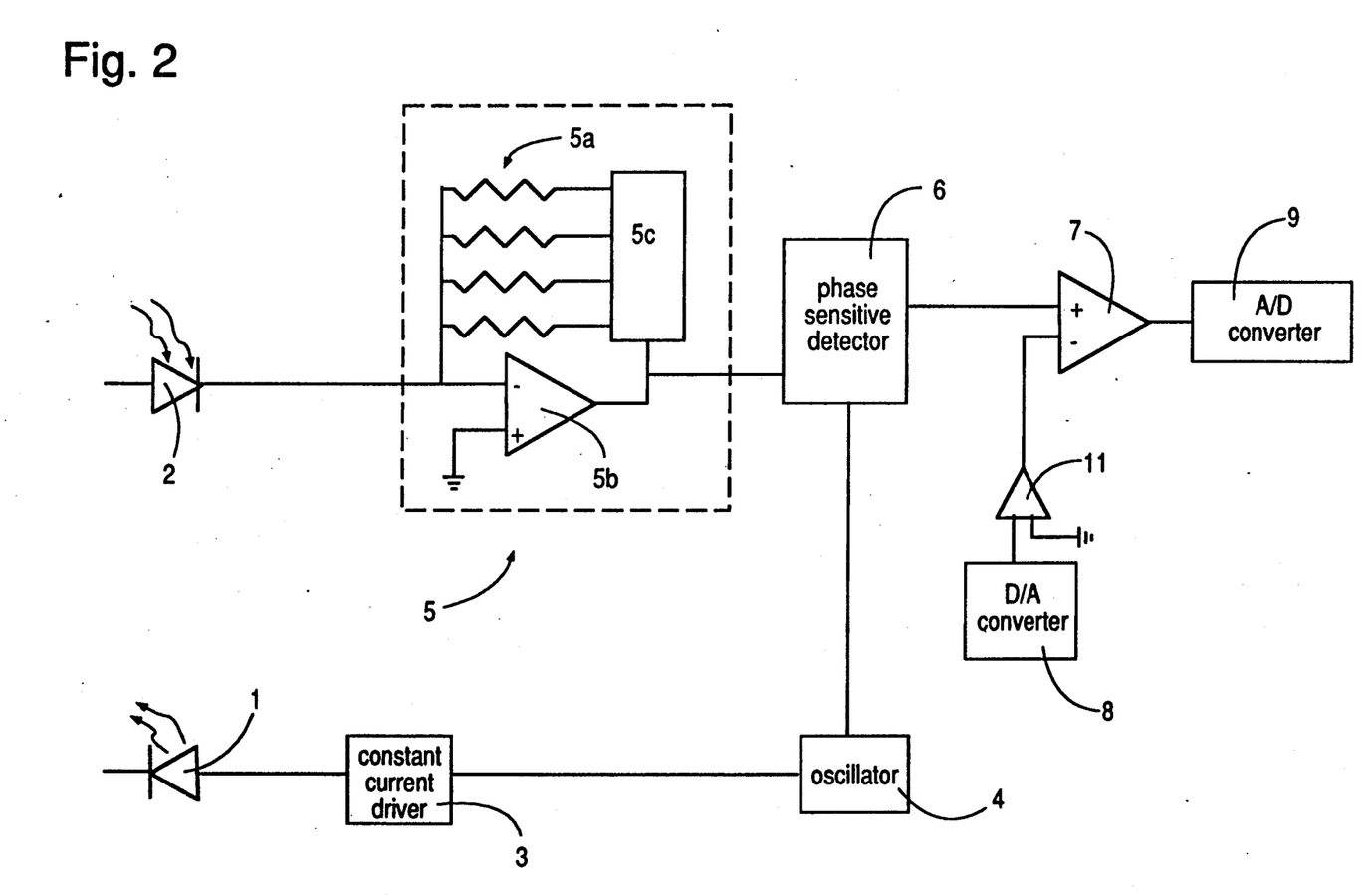
FIG. 2 is a block diagram of a sensor board according to one embodiment of this invention.

FIG. 2 is a block diagram indicating the various components which comprise a sensor board according to one embodiment of this invention, along with an LED and a photodetector.

The light-emitting diode (LED) 1 emits light which is reflected from a substrate (not shown). The reflected light is detected by photodiode 2 which generates an electrical signal proportional to the intensity of the reflected light. Photodiode 2 is, for example, a planar silicon diode such as model BPX 61 or Model BPW 34F manufactured by Siemens.

Of importance, the LED preferably used with this invention produces light having a wavelength in the near infrared, preferably between 880 and 950 nanometers, such as a model LD 261 or SFH 481 LED manufactured by Siemens. This wavelength range was selected because it is transmitted through most photoresists, most oxides and most nitrides used in semiconductor wafer processing. Light in the range 880–950 nanometers is not absorbed by these materials and not reflected by these materials but rather is reflected by the interfaces between these materials where the refractive indexes of the two materials change. Naturally, should other materials be monitored during processing in accordance with this invention other light sources having different wavelengths selected to be optimal for the typical process being monitored can be used.

Figure 3:
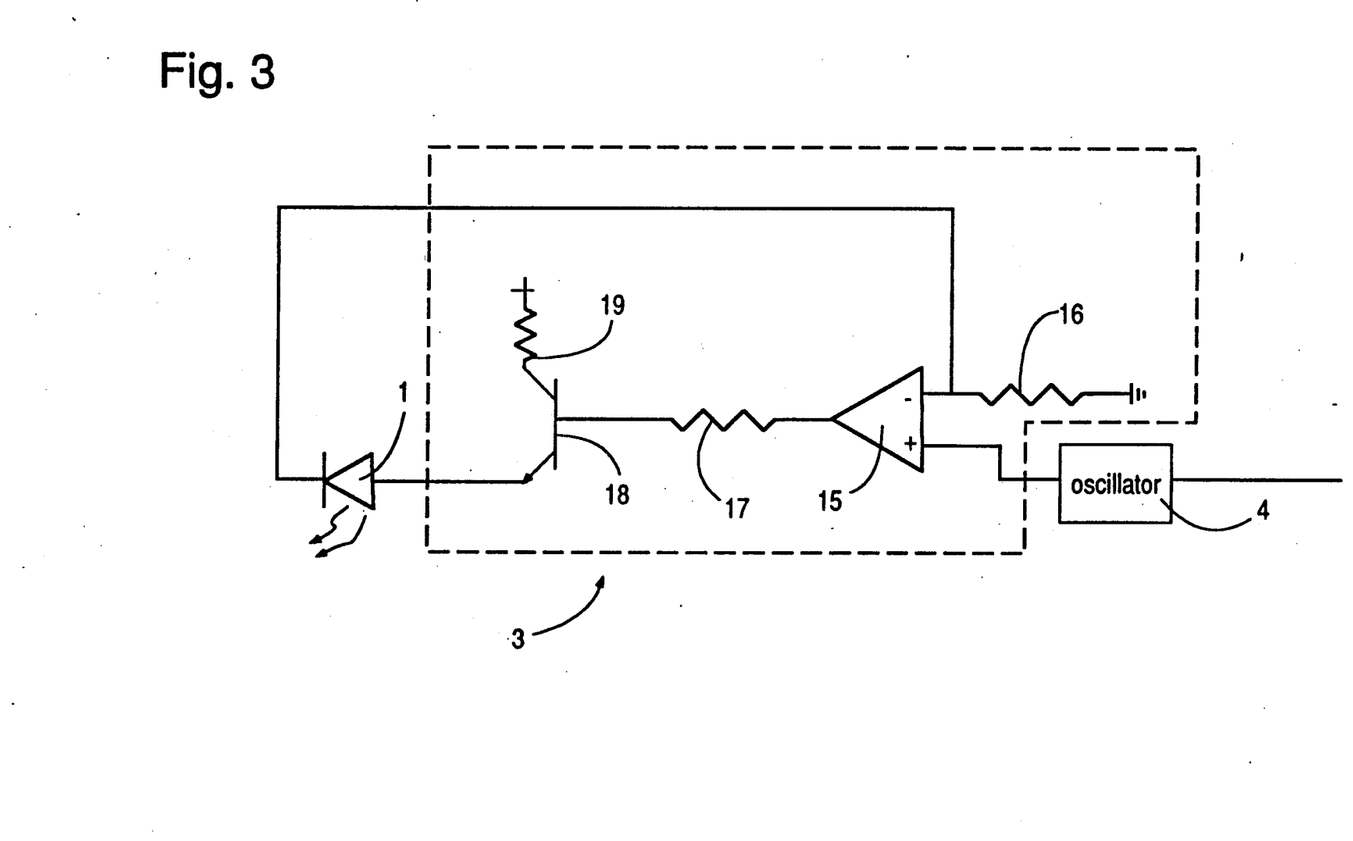
FIG. 3 is a schematic diagram of the components of the constant current driver.

The current to LED 1 is supplied by constant current driver 3 which eliminates fluctuations in LED intensity due to ambient temperature fluctuations. This feature helps eliminate noise in the final signal. As shown in FIG. 3, constant current driver 3 is built from operational amplifier 15, typically model TL072 manufactured by Texas Instruments, resistors 16 and 17 each having a resistance of about 100Ω, resistor 19 having a resistance of about 200Ω and transistor 18 such as model 2N4013 manufactured by Motorola. Oscillator 4 which is, for example, model LM555 manufactured by National Semiconductor, feeds one input of operational amplifier 15 which controls the base of transistor 18.

LED 1 is in the feedback loop of operational amplifier 15.

In one embodiment of this invention, constant current driver 3 may supply current to and control up to four LEDs. A controller (not shown) which is a semiconductor device such as model ADG528 manufactured by Analog Devices receives an input from resistor 17. Four output lines of the controller each control the base of one transistor identical to transistor 18. Each of the four transistors will supply current to one LED and all four LEDs will be in the feedback loop of operational amplifier 15.

Referring to FIG. 2 the electrical signal produced by photodetector 2 goes to an I/V converter 5, which provides two functions. Firstly, I/V convertor 5 converts the current generated by photodiode 2 to a voltage. Secondly, it is software programmable to allow real time autoscaling under computer control referred to as automatic gain control. Typically, a resistor is chosen from the group 5a of four resistors by programmable selector 5c. The chosen resistor is positioned in the feedback loop of operational amplifier 5b, thus enabling first-stage gain to either maximize the signal for further processing or to prevent saturation of strong signals as is necessary.

Although the group 5a of resistors typically consists of four resistors each having a different value of resistance such as 200KΩ, 500KΩ, 1MΩ and 2MΩ, any suitable number of resistors having a variety of resistances may be used. Operational amplifier 5b is, for example model TL072 manufactured by Texas Instruments. Programmable selector 5c which may be model AD7590 manufactured by Analog Devices is software programmable to choose the most desirable resistor from group 5a as described below.

Phase-sensitive detector 6 enables the synchronization of the detected signal and LED 1. LED 1 receives a pulsed signal through constant current driver 3 from oscillator 4 which switches LED 1 on and off. The pulse of light emitted by LED 1 is reflected by a substrate and detected by photodiode 2 as a pulse of light. Oscillator 4 also operates phase-sensitive detector 6 such that the pulsed signal generated by photodetector 2 and fed to phase sensitive detector 6 through I/V converter 5 is known to correspond to light emitted by LED 1 and reflected by the substrate plus ambient background light. Any signal generated by photodetector 2 when LED 1 is off is known to correspond only to ambient background light. The difference between the signal caused by ambient light when LED 1 is off and the signal caused by reflected light plus ambient light when LED 1 is on gives the true signal which is caused by the reflected light alone.

Figure 4:
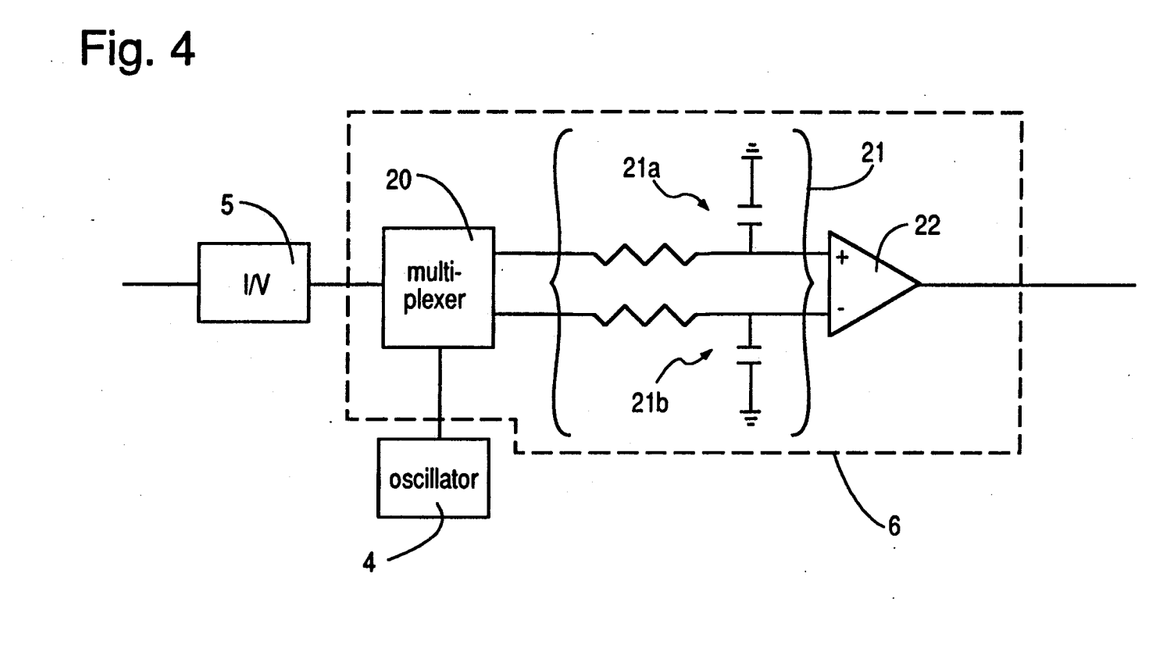
FIG. 4 is a schematic diagram of the components of the phase sensitive detector.

Oscillator 4 facilitates the subtraction of the detected signal when LED 1 is off from the detected signal when LED 1 is on by controlling phase sensitive detector 6 in the following manner. As shown in FIG. 4 phase sensitive detector 6 comprises three key components, multiplexer 20 which may be, for example, multiplexer model AD7592 manufactured by Analog Devices, RC network 21 and programmable gain amplifier 22 which typically consists of two components (not shown), a difference amplifier such as AD524 manufactured by Analog Devices and a software programmable gain selector such as AD7590 manufactured by Analog Devices. The capacitors of RC network 21 typically have a capacitance of 0.1 μf and the resistors typically have a resistance of 100KΩ. When oscillator 4 turns on LED 1 a corresponding signal is sent to multiplexer 20. Multiplexer 20 feeds the output from I/V converter 5 to one RC circuit, either 21a or 21b, each of which is one input to programmable gain amplifier 22. When oscillator 4 turns off LED 1, oscillator 4 also causes multiplexer 20 to switch the output from I/V converter 5 to the other RC circuit, either 21a or 21b. Consequently, the signal produced by photodiode 2 and I/V converter 5 with LED 1 off is fed to the input of programmable gain amplifier 22 not used when LED 1 is on.

Programmable gain amplifier (PGA) 22 outputs the difference between the detected signal when LED 1 is on, which is one input to PGA 22, and the detected signal when LED 1 is off, which is the other input to PGA 22, to provide the true signal caused by the light produced by LED 1 and reflected from a substrate. Programmable gain amplifier 22 also amplifies this true, difference signal by a gain of either 1 (no amplification), 10, 100 or 1000. The choice of gain is software controlled as described below.

Programmable gain amplifier 22 of phase sensitive detector 6 feeds one input of programmable gain amplifier 7 in FIG. 2. Programmable gain amplifier 7 consists of two components, (not shown) a difference amplifier such as AD524 manufactured by Analog Devices and a software programmable gain selector such as AD7590, also manufactured by Analog Devices.

Digital to analog (D/A) converter 8 feeds the other input of programmable gain amplifier 7 through operational amplifier 11 which may be, for example, operational amplifier LF 147 manufactured by National Semiconductor. D/A converter 8, which is programmable, may be AD7537 manufactured by Analog Devices.

Programmable gain amplifier 7 subtracts the computer-controlled voltage offset produced by D/A converter 8 from the signal produced by programmable gain amplifier 22. This subtraction removes the large DC background from the detected signal. Additional amplification of the difference signal by 1, 10, 100 or 1000 times can be selectively provided by programmable gain amplifier 7, although a gain of 1000 will usually generate a signal having too much noise to provide practical measurements. By removing the DC background and amplifying the difference, resolution is increased and a signal is provided in which previously small changes are larger and more clearly detected.

Figure 5A:
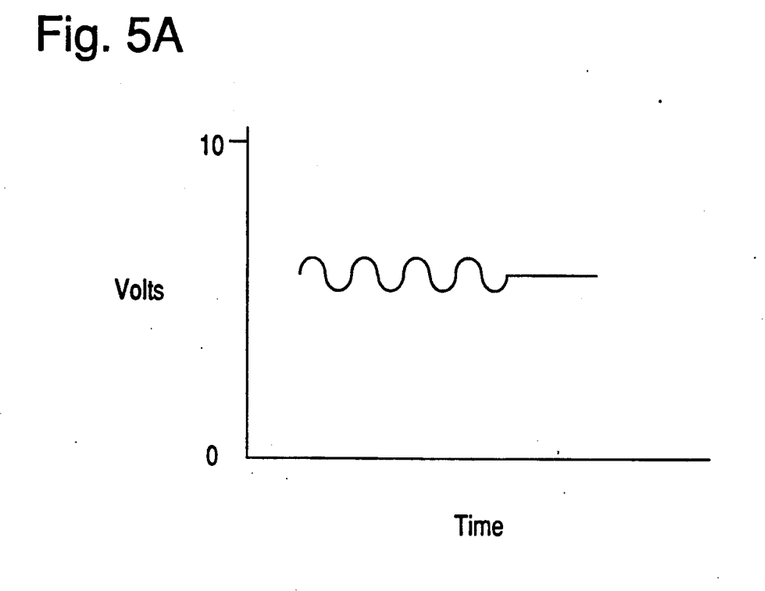
FIG. 5A represents an example of an oscillating signal to which the offset and amplification of this invention have not been applied.
Figure 5B:
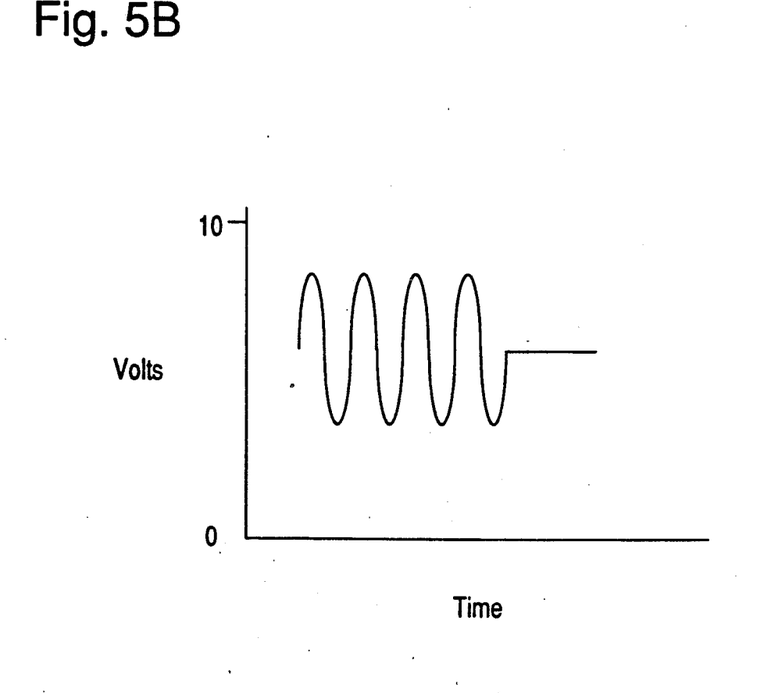
FIG. 5B represents an example of an oscillating signal to which the offset and amplification of this invention have been applied.

FIG. 5A represents an example of an oscillating signal with a large DC background. No offset or additional amplification has been applied to this signal. FIG. 5B represents a possible example of the signal of FIG. 5A from which the DC background has been subtracted using the offset provided by D/A converter 8 and which has also been amplified. The range of the signal oscillation has been greatly extended. Changes in the oscillation of a signal represented by FIG. 5B are much more easily and accurately detected than the signal oscillations of FIG. 5A. It is the combination of offset and amplification that provides the expanded signal of FIG. 5B.

The amplified difference signal which is output from programmable gain amplifier 7 is then converted by an analog to digital converter 9 to a sequence of 12 bit digital numbers, each number representing one sample of the amplified 12 bit difference signal. A/D converter 9 may be, for example, model AD574 manufactured by Analog Devices. A track/hold component (not shown) such as AD585AQ manufactured by Analog Devices may be included, as part of A/D converter 9 for keeping the incoming signal at a desired level.

A/D converter 9 allows data acquisition at a rate greater than 1000 samples per second. From A/D converter 9 the data is fed to a computer for further manipulation and displayed as described in the copending application entitled "Method for Endpoint Detection and Structure Therefor," inventors Steven C. Leach, Jewett W. Fowler, Herbert E. Litvak, and Mariste A. Thomson U.S. Ser. No. 07/579,056, filed the same day as this application and incorporated here by reference.

The algorithm for selecting the gain applied to the signal generated by photodetector 2, called the automatic gain control (AGC) will now be described. During a period of time called the AGC time and selected by the user as described in the Xinix 2200 User's Manual, the sample produced by A/D converter 9 which represents the voltage $V_{AD}$ fed to A/D converter 9 is measured and adjusted. A feedback resistor from group 5a and a gain setting $G_1$ for programmable gain amplifier 22 are chosen to adjust $V_{AD}$ to a level between 1.1 and 5 volts. This measurement-adjustment cycle typically takes 0.1 seconds and a maximum of three cycles may be required to achieve the desired level of $V_{AD}$. A suitable level of $V_{AD}$ may be different than the desired level indicated here.

Programmable gain amplifier 7 does not apply any amplification at this stage of signal processing. Its gain is set at one until a voltage offset from D/A converter 8 is applied during data acquisition.

If the first measurement of $V_{AD}$ is above or below a limit past which the desired $V_{AD}$ can be achieved by applying the available gain settings, an error message such as "too much signal" or "too little signal" will be terminated.

The algorithm which changes the feedback resistor and gain setting of programmable gain amplifier 22 is table driven for simplicity. The four feedback resistors in the group 5a of I/V converter 5 have resistance values of 200KΩ 500KΩ, 1MΩ and 2MΩ. Programmable gain amplifier (PGA) 22 can amplify an input signal by a factor $G_1$ of 1, 10, 100 or 1,000.

Table 1 lists the overall gain values that can be applied to the signal originating from photodetector 2 and the feedback resistor and $G_1$ values that are chosen to achieve the desired overall gain value. Although a gain over 500 million can theoretically be achieved using this invention, it is not practical to amplify the current produced by photodetector 2 any more than this. A gain of 500 million applied to a 10 nA current converts that current to a 5V potential which is in the desired range. Because the dark current generated by photodetector 2, the current when no light is detected, is 2 nA, measurement of a current any smaller than 10 nA becomes obscured by noise due to the dark current.

TABLE 1

| Overall Gain | RΩ | G1 of PGA 22 |
|---|---|---|
| 200,000 | 200K | 1 |
| 500,000 | 500K | 1 |
| 1,000,000 | 1M | 1 |
| 2,000,000 | 2M | 1 |
| 5,000,000 | 500K | 10 |
| 10,000,000 | 1M | 10 |
| 20,000,000 | 2M | 10 |
| 50,000,000 | 500K | 100 |
| 100,000,000 | 1M | 100 |
| 200,000,000 | 2M | 100 |

TABLE 1-continued

| Overall Gain | RΩ | G1 of PGA 22 |
|---|---|---|
| 500,000,000 | 500K | 1000 |

Some overall gain values can be achieved using either of two combinations of resistance and $G_1$ values. For instance, both a resistance of 200KΩ plus a $G_1$ of 10 and a resistance of 2MΩ plus a G of 1 will result in an overall gain of two million. In such cases, Table 1 is set to choose the option with the higher resistance value and the lower $G_1$ value because this option produces an amplified signal having a lower noise level.

Figure 6:
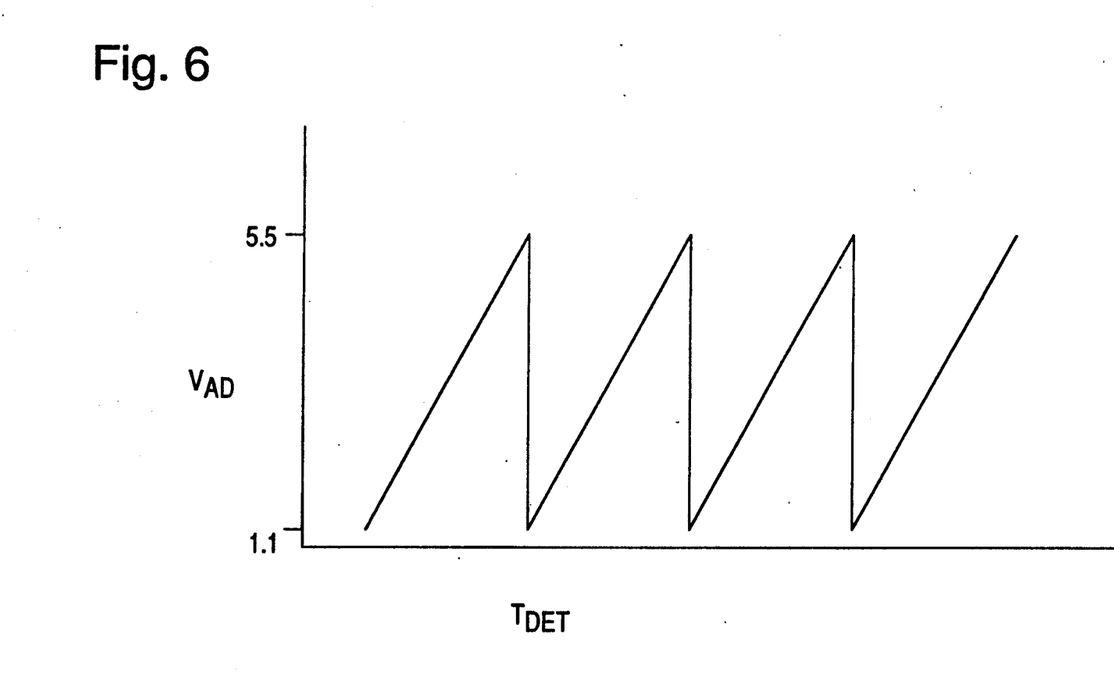
FIG. 6 is a graph of current produced by a photodetector, $I_{DET}$ vs. the voltage $V_{AD}$ resulting from automatic gain control.

Using automatic gain control as described above produces the profile of $V_{AD}$ shown in FIG. 6. $I_{DET}$ is the current generated by photodetector 2. As the current $I_{DET}$ increases $V_{AD}$ increases and the same overall gain value is used until the $V_{AD}$ value reaches a predetermined maximum, in this case 5.5 volts. At that point a lower overall gain value is chosen so that $V_{AD}$ again drops to 1.1 volts. Each sawtooth in FIG. 6 represents one gain stage.

The resistance and $G_1$ values which are in effect at the end of AGC time will remain in effect throughout data acquisition. Although this algorithm has been described in relation to particular overall gain values, the possible overall gain values will depend on the feedback resistors of I/V converter 5 and the $G_1$ values of programmable gain amplifier 22 which are available on the sensor board. The available resistance and gain values may vary from those reported here.

In accordance with this invention, three algorithms are used for processing the signal with offset and amplification to increase resolution as described above. The general algorithm takes the input signal which has been amplified according to the automatic gain control algorithm and subtracts from the input signal a selected offset. The offset is stored digitally and converted to an analog signal by D/A converter 8 prior to being combined with the input signal produced by phase sensitive detector 6 at programmable gain amplifier 7. The resulting difference signal is then amplified by a selected amount (typically by unity or a factor of 10 or 100 depending upon certain criteria in the algorithm) and the resulting signal is input to A/D converter 9.

In the first variation of this general algorithm, the offset voltage subtracted from the input signal is zero and the amplification factor is 1. In this case each sample of the amplified difference signal output by A/D converter 9 is a measure of a corresponding sample of the input signal which originated at photodetector 2 and was processed by I/V converter 5 and phase sensitive detector 6 to 12 bit accuracy.

In the second variation of the general algorithm the offset voltage subtracted from the input signal has an amplitude given by the previous sample of the input signal less a fixed voltage typically of 0.5 volts. Accordingly, the signal produced by programmable gain amplifier 7 without any amplification has a magnitude of about 0.5 volts. The gain of the system is set to a factor of 10 thereby increasing the amplitude of the signal produced by programmable gain amplifier 7 to 5 volts. The amplified signal of 5 volts is then converted to a series of digital samples by A/D converter 9, each sample being presented by 12 bits. However, the equivalent bit accuracy of the resulting samples is between 15 and 16 bits because of the amplification by a factor of 10 (10 has an amplitude between $2^3$ and $2^4$ and thus the actual bit equivalency is somewhere between 15 (12+3) and 16 (12+4) bits). By this technique resolution of the detected signal is increased.

The third variation of this general algorithm subtracts from the signal processed by phase sensitive detector 6 a voltage having an amplitude given by the previous signal less 0.05 volts. Thus the output signal from the programmable gain amplifier 7 before gain has been applied is about 0.05 volts. This output signal is then amplified by a factor of 100 by programmable gain amplifier 7 so that the final output signal will still be about 5V. The signal resulting from the 12 bit A/D converter 9 has an accuracy which would typically be given by an analog to digital converter producing a 18 to 19 bit digital word for example (an amplification of a hundred is between $2^6$ and $2^7$ and therefore the bit equivalency of its sample is between 18 (12+6) to 19 (12+7) bits).

Figure 7:
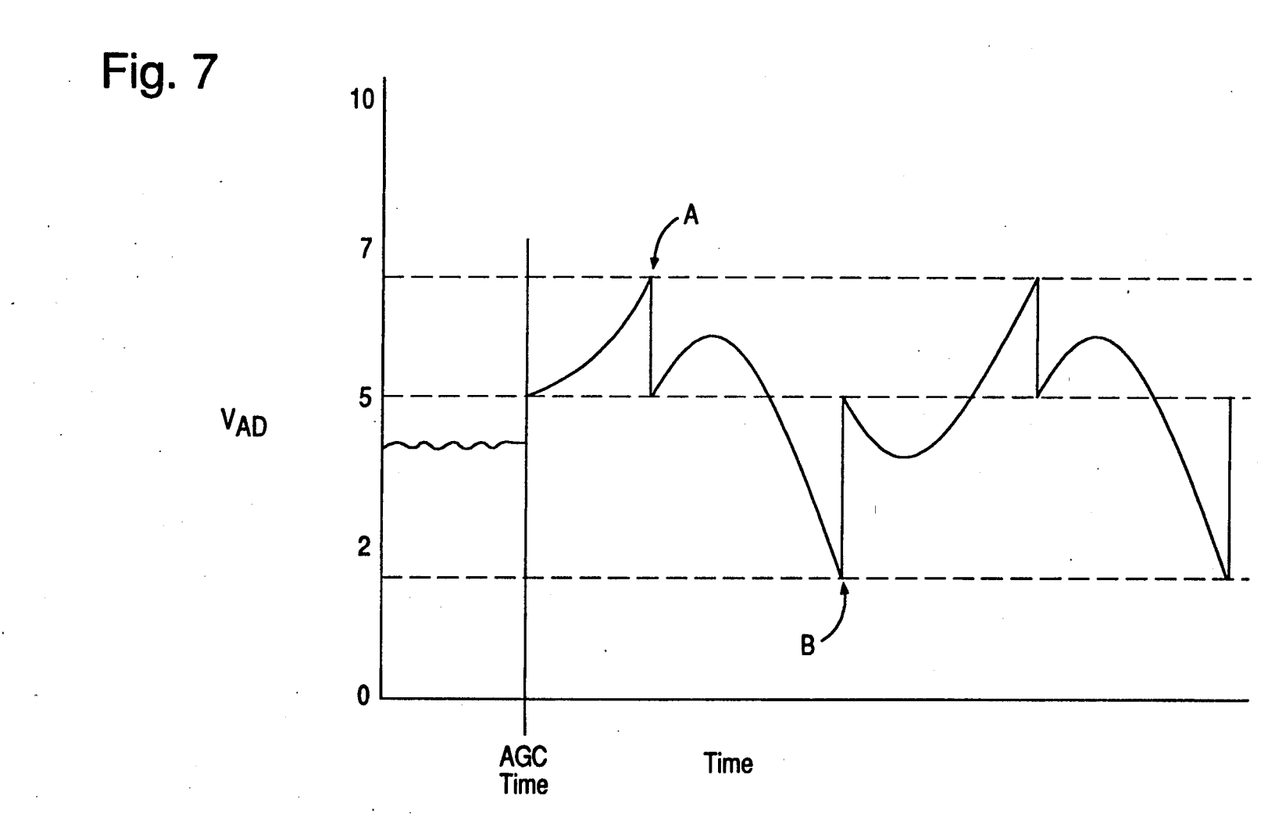
FIG. 7 is an example of the way in which $V_{AD}$ may be affected by offset and amplification according to one embodiment of the invention.

FIG. 7 helps to illustrate how the offset is controlled in the second and third variations of the general algorithm. In both variations the offset and amplification combine to initially produce $V_{AD}$ of about 5V at the end of AGC time. The offset is held constant so that if the input signal increases, $V_{AD}$ will increase also. When $V_{AD}$ reaches a predetermined maximum value $V_{ADH}$, as it does at point A, the offset is readjusted to bring $V_{AD}$ to 5V again. Similarly, the offset is held constant until $V_{AD}$ reaches a minimum value $V_{ADL}$, as it does at point B, and is then readjusted to bring $V_{AD}$ to 5V again.

$V_{ADH}$ and $V_{ADL}$ are typically 10V and 1V, and preferably 7V and 2V, respectively. The signal fed into A/D converter 9 must be kept within a desired range dependant on the particular A/D converter used.

The signal $V_{AD}$ is manipulated to provide a display which is representative of the light reflected by the monitored substrate as described in copending application "Method for Endpoint Detection."

The 1000 gain setting which is available with programmable gain amplifier 7 is typically not used due to the increased noise associated with such high amplification.

According to one embodiment of this invention, the algorithm senses when more resolution is required because it does not detect an expected trend in the signal such as an upward slope, a downward slope or oscillations. The algorithm then implements the second, and if necessary the third variation to increase resolution of the signal.

The system described above is in essence an adaptive controller producing proportional integrated differential control.

Figure 8:
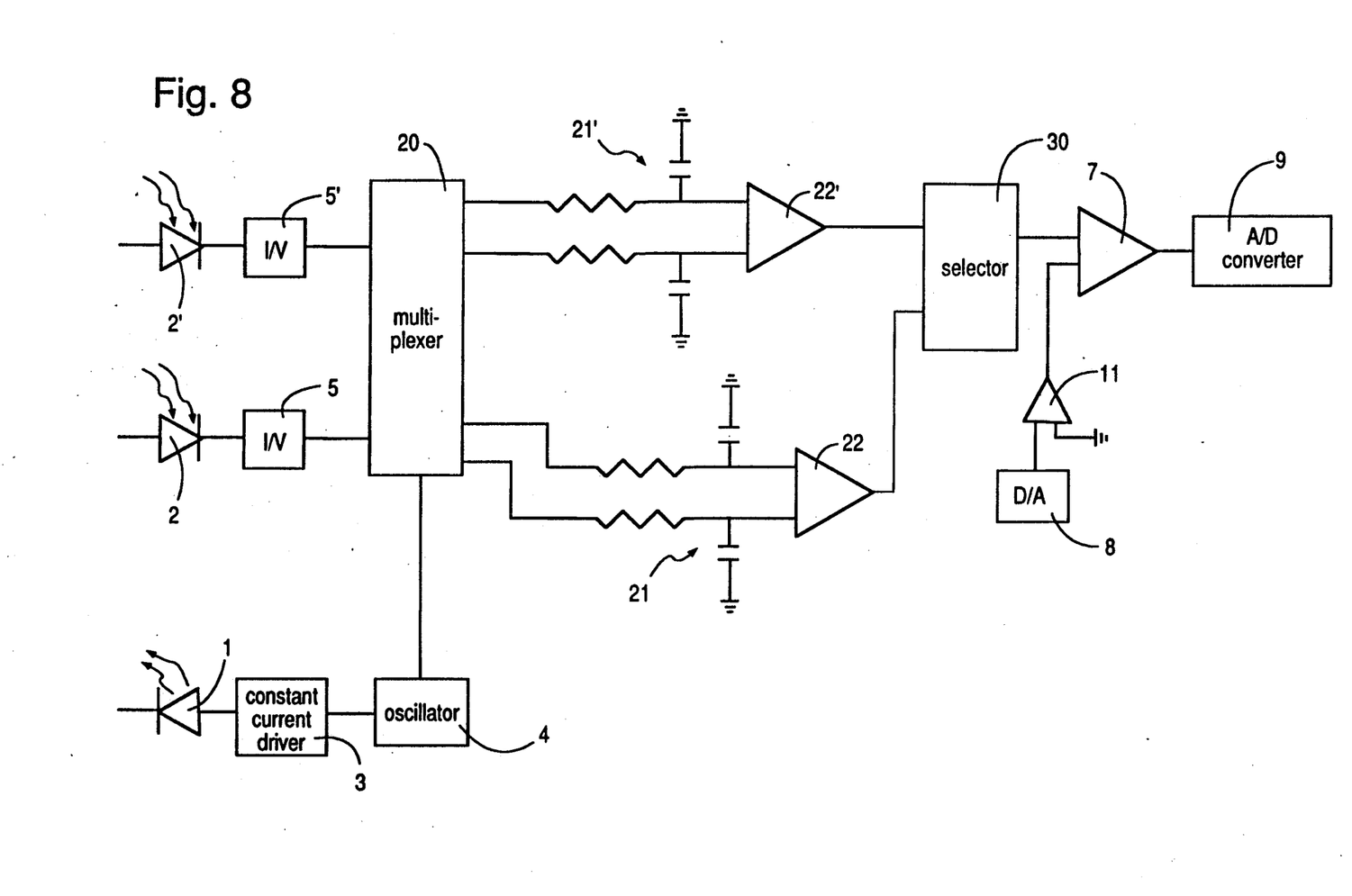
FIG. 8 is a block diagram of an embodiment of this invention utilizing two photodetectors.

Another embodiment of this invention is illustrated in FIG. 8. Sensor board components of FIGS. 2-4 are designated by the same reference numbers. Two separate photodetectors 2 and 2' monitor the light reflected by a substrate from the same LED 1 source. Preferably one photodetector is placed on either side of LED 1 so that each photodetector 2 and 2' monitors a different portion of the light reflected from the substrate.

The current generated by each photodetector 2 and 2' is converted to a voltage and amplified by a separate I/V converter 5 or 5' respectively. The output from both I/V converters is fed to the same multiplexer 20 which is controlled by an oscillator 4 in the manner described above. The signals originating from the two photodetectors 2 and 2' remain separate in RC circuits 21 and 21' and programmable gain amplifiers 22 and 22' where the separate signals are manipulated as described above. Both signals supply inputs to a selector 30 which may be, for instance, model ADG526A manufactured by Analog Devices. Selector 30 chooses one of the two signals to feed to programmable gain amplifier 7 for further processing. Selector 30 alternates the output at a rate sufficient for the 12 bit digitized samples produced by A/D converter 9 to alternate or nearly alternate between representing the signal originating at each photodetector, 2 and 2'. When groups of digitized samples are averaged as described in copending application "Method of Endpoint Detection" the average of the group will represent the combination of the signals from the two photodetectors.

An average of the two signals may result in a signal with decreased noise. This technique is especially helpful in decreasing noise caused by wafer wobble.

We claim:

1. An apparatus comprising:
   a light source for providing light to be reflected from a substrate on which a chemical processing operation is performed;
   means for converting said light reflected from said substrate to an electrical signal;
   means for providing a plurality of gain settings for amplifying said electrical signal;
   means for choosing one of said plurality of gain settings for amplifying said electrical signal;
   means for amplifying said electrical signal to produce an amplified electrical signal within a predetermined range; and
   means for monitoring said amplified electrical signal so as to detect changes in the intensity of said reflected light.

2. The sensor board according to claim 1 further comprising:
   means for alternately switching said light source on an off whereby said means for converting said light reflected from said substrate to an electrical signal produces a first electrical signal when said light source is on and a second electrical signal when said light source is off; and
   means for subtracting said first electrical signal from said second electrical signal to produce a difference signal such that said difference signal is amplified by said means for amplifying to produce an amplified difference signal.

3. The sensor board according to claim 1 further comprising:
   means for subtracting an offset from said amplified electrical signal to produce a difference signal; and
   means for amplifying said difference signal to produce an amplified difference signal in a predetermined range.

4. A sensor board for processing electrical signals comprising:
   means for receiving an electrical current;
   means for converting said electrical current to a voltage;
   means for causing said electrical current to alternate between a high state and a low state such that said voltage alternates between a high state and a low state;
   means for subtracting said voltage in said low state from said voltage in said high state to produce a difference voltage;

means for amplifying said difference voltage to produce an amplified difference voltage in a predetermined range; and means for monitoring said amplified difference voltage so as to detect changes in the magnitude of said electrical current.

5. The sensor board for processing electrical signals according to claim 4 wherein said sensor board is installed in an endpoint controller for detecting the endpoint of a chemical processing operation.

6. The sensor board for processing electrical signals of claim 4 wherein said means for causing said electrical current to alternate between a high state and a low state comprises:

a light source for transmitting light to a surface which reflects some portion of said light;

means for generating said electrical current from said reflected light; and means for switching said light source on and off at regular intervals whereby said electrical current is in said high state when said light source is on and said electrical current is in said low state when said light source is off.

7. The sensor board for processing said electrical signals according to claim 6 wherein said light source is a light emitting diode having an operating current supplied by a constant current driver.

8. The sensor board according to claim 7 wherein said light source is a plurality of light emitting diodes, the operating current of each light emitting diode being supplied by a constant current driver.

9. The sensor board according to claim 6 wherein said means for generating electrical current is a photodiode.

10. The sensor board for processing electrical signals according to claim 6 wherein said means for converting said electrical current to a voltage comprises:

an operational amplifier having a feedback loop; and a plurality of resistors positioned in said feedback loop, each resistor having a different resistance value; and means for choosing one of said resistors whereby said electrical current is converted to a voltage and amplified.

11. A sensor board for processing electrical signals comprising:

means for receiving an electrical current;

means for converting said electrical current to a voltage, said converting means comprising an operational amplifier having a feedback loop, a plurality of resistors positioned in said feedback loop, each resistor having a different resistance value, and means for choosing one of said resistors such that said electrical current is converted to a voltage and amplified;

means for causing said electrical current to alternate between a high state and a low state, such that said voltage alternates between a high state and a low state, comprising a light source for transmitting light to a surface which reflects some portion of said light, a means for generating said electrical current from said reflected light, and a means for switching said light source on and off at regular intervals such that said electrical current is in said high state when said light source is on and said electrical current is in said low state when said light source is off;

means for subtracting said voltage in said low state from said voltage in said high state to produce a difference voltage comprising a multiplexer having a first input from said means for switching said light source and a second input from said operational amplifier, said multiplexer having a first output and a second output, said first output being a first input to a programmable gain difference amplifier and said second output being a second input to said programmable gain difference amplifier, said programmable gain difference amplifier having an amplifier output supplying the difference of said first input from said second input, said means for switching said light source causing said multiplexer to apply said voltage in said low state to said first output and said voltage in said high state to said second output such that said programmable gain difference amplifier subtracts said voltage in said low state from said voltage in said high state to produce said difference voltage; and means for amplifying said difference voltage to automatically produce an amplified difference voltage in a predetermined range.

12. A sensor board for processing electrical signals according to claim 11 further comprising:

a second programmable gain difference amplifier having a third input and a fourth input, said third input receiving said amplified difference voltage; and a digital to analog converter for supplying said voltage offset to said fourth input such that said second programmable gain difference amplifier subtracts said voltage offset from said amplified difference voltage to produce a second difference voltage, said second programmable gain difference amplifier also amplifying said second difference voltage to produce a second amplified difference voltage in a second predetermined range.

13. A sensor board for processing electrical signals comprising:

a light source for transmitting light to a surface which reflects some portion of said light;

a first photodiode for generating a first electrical current from reflected light;

a second photodiode for generating a second electrical current from reflected light;

means for switching said light source on and off at regular intervals whereby said first and second electrical currents are in a high state when said light source is on and said first and second electrical currents are in a low state when said light source is off;

means for converting said first electrical current to a first voltage whereby said first voltage alternates between a high state and a low state;

means for converting said second electrical current to a second voltage whereby said second voltage alternates between a high state and a low state;

means for subtracting said first voltage in said low state from said first voltage in said high state to produce a first difference voltage;

means for amplifying said first difference voltage to produce a first amplified difference voltage in a first predetermined range;

means for subtracting said second difference voltage in said low state from said second difference voltage in said high to produce a second difference voltage;

means for amplifying said second difference voltage to produce a second amplified difference voltage;

said first amplified difference voltage and said second amplified difference voltage being applied to a selector, said selector alternately outputting said first amplified difference voltage and said second amplified difference voltage;

means for alternatively subtracting a voltage offset from said first and said second amplified difference voltages to produce a third and a fourth difference voltage; and means for amplifying said third and said fourth difference voltage to produce a third and a fourth amplified difference voltage.

14. A sensor board for processing electrical signals in an endpoint controller for detecting the endpoint of a chemical processing operation comprising:

means for receiving an electrical current;

means for converting said electrical current to a voltage;

means for causing said electrical current to alternate between a high state and a low state such that said voltage alternates between a high state and a low state;

means for subtracting said voltage in said low state from said voltage in said high state to produce a difference voltage;

means for amplifying said difference voltage to automatically produce an amplified difference voltage in a predetermined range;

means for subtracting a voltage offset from said amplified difference voltage to produce a second difference voltage; and means for amplifying said second difference voltage to produce a second amplified difference voltage in a second predetermined range.

15. A method for detecting the endpoint of a chemical processing operation on a substrate by monitoring changes in light intensity of light reflected from said substrate comprising the steps of:

providing a light source, so that said light reflects from said substrate;

converting said light reflected from said substrate to an electrical signal;

providing a plurality of gain settings for amplifying said electrical signal;

choosing one of said plurality of gain settings for amplifying said electrical signal; and amplifying said electrical signal to produce an amplified electrical signal within a predetermined range.

16. The method according to claim 15 further comprising the steps of:

switching said light source on and off such that said step of converting said light reflected from said substrate to an electrical signal produces a first electrical signal when said light source is on and a second electrical signal when said light source is off; and subtracting said first electrical signal from said second electrical signal to produce a difference signal such that said difference signal is amplified by said means for amplifying to produce an amplified difference signal.

17. The method according to claim 15 further comprising the steps of:

subtracting an offset from said amplified electrical signal to produce a difference signal; and amplifying said difference signal to produce an amplified difference signal in a predetermined range.

18. A method for processing electrical signals comprising the steps of:

receiving an electrical current;

converting said electrical current to a voltage;

causing said electrical current to alternate between a high state and a low state such that said voltage alternates between a high state and a low state;

subtracting said voltage in said low state from said voltage in said high state to produce a difference voltage; and amplifying said difference voltage to automatically produce an amplified difference voltage in a predetermined range.

19. The method for processing electrical signals according to claim 18 further comprising:

subtracting a voltage offset from said amplified difference voltage to produce a second difference voltage; and amplifying said second difference voltage to produce a second amplified difference voltage in a second predetermined range.

20. The method for processing electrical signals of claim 18 wherein the step of causing said electrical current to alternate between a high state and a low state comprises the steps of:

transmitting light to a surface which reflects some portion of said light;

generating said electrical current from said reflected light; and switching said light source on and off at regular intervals such that said electrical current is in said high state when said light source is on and said electrical current is in said low state when said light source is off.

21. The method for processing said electrical signals according to claim 20 further comprising the step of supplying operating current to said light source by a constant current driver.

22. The method according to claim 18 further comprising the step of supplying operating current to a plurality of said light sources by a constant current driver.

23. The method according to claim 18 further comprising the step of generating electrical current with a photodiode.

24. The method for processing electrical signals according to claim 18 wherein the step of converting electrical current to a voltage comprises:

amplifying said electrical current and feeding back said amplified electrical current to be reamplified; and positioning a plurality of resistors in said feedback loop, each resistor having a different resistance value; and choosing one of said resistors such that said electrical current is converted to a voltage and amplified.

25. The method for processing electrical signals according to claim 24 wherein subtracting said voltage in said low state from said voltage in said high state comprises:

inputting to a multiplexer a first input from said means for switching said light source and a second input from said operational amplifier;

outputting from said multiplexer a first output and a second output;

inputting to a programmable gain difference amplifier a first input being a first output from said multiplexer and a second input being said second output from said multiplexer;

outputting from said programmable gain difference amplifier the amplified difference of said first input from said second input; and switching said light source so as to cause said multiplexer to apply said voltage in said low state to said first output and said voltage in said high state to said second output, such that said programmable gain difference amplifier subtracts said voltage in said low state from said voltage in said high state to produce said difference voltage.

26. A method for processing electrical signals according to claim 25 further comprising the steps of:

inputting to a second programmable gain difference amplifier a third input and a fourth input, said third input receiving said amplified difference voltage; and supplying said voltage offset from a digital to analog converter to said fourth input such that said second programmable gain difference amplifier subtracts said voltage offset from said amplified difference voltage to produce a second difference voltage, said second programmable gain difference amplifier also amplifying said second difference voltage to produce a second amplified difference voltage in a second predetermined range.

27. A method for processing electrical signals comprising:

transmitting a light source to a surface which reflects some portion of said light;

generating from a first photodiode a first electrical current from reflected light;

generating from a second photodiode a second electrical current from reflected light;

switching said light source on and off at regular intervals such that said first and second electrical currents are in a high state when said light source is on and said first and second electrical currents are in a low state when said light source is off;

converting said first electrical current to a first voltage such that said first voltage alternates between a high state and a low state;

converting said second electrical current to a second voltage such that said second voltage alternates between a high state and a low state;

subtracting said first voltage in said low state from said first voltage in said high state to produce a first difference voltage;

amplifying said first difference voltage to produce a first amplified difference voltage in a first predetermined range;

subtracting said second difference voltage in said low state from said second difference voltage in said high to produce a second difference voltage;

amplifying said second difference voltage to produce a second amplified difference voltage;

applying said first amplified difference voltage and said second amplified difference voltage to a selector, said selector alternately outputting said first amplified difference voltage and said second amplified difference voltage;

alternatively subtracting a voltage offset from said first and said second amplified difference voltages to produce a third and a fourth difference voltage; and amplifying said third and said fourth difference voltage to produce a third and a fourth amplified difference voltage.

* * * * *

UNITED STATES PATENT AND TRADEMARK OFFICE
CERTIFICATE OF CORRECTION

PATENT NO. : 5,138,149
DATED : August 11, 1992
INVENTOR(S) : Raymond J. Cadet et al.

It is certified that error appears in the above-identified patent and that said Letters Patent is hereby corrected as shown below:

Column 7, Line 10, delete "07/579,056", and insert --07/578,056, now U.S. Patent 5,190,614 issued on March 2, 1993,--.

Column 8, line 9, delete "G" and insert --$G_1$--.

Column 10, line 39, claim 2, delete "an" and insert --and--.

Column 11, line 38, claim 10 delete "."

Signed and Sealed this

Third Day of January, 1995

*Attest:*

BRUCE LEHMAN

*Attesting Officer*     *Commissioner of Patents and Trademarks*